US010030217B2

(12) United States Patent
Mayer et al.

(10) Patent No.: US 10,030,217 B2
(45) Date of Patent: Jul. 24, 2018

(54) SOLID TEXTILE CARE AND/OR SKINCARE COMPOSITION

(75) Inventors: Konstanze Mayer, Duesseldorf (DE); Karl-Heinz Scheffler, Duesseldorf (DE); Rene-Andres Artiga Gonzalez, Duesseldorf (DE); Mario Sturm, Leverkusen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 12/465,759

(22) Filed: May 14, 2009

(65) Prior Publication Data

US 2009/0281011 A1 Nov. 12, 2009

Related U.S. Application Data

(63) Continuation of application No. PCT/EP2007/060812, filed on Oct. 11, 2007.

(30) Foreign Application Priority Data

Nov. 16, 2006 (DE) ........................ 10 2006 054 436

(51) Int. Cl.
| | | |
|---|---|---|
| *C11D 17/00* | (2006.01) | |
| *C11D 3/00* | (2006.01) | |
| *C11D 3/04* | (2006.01) | |
| *C11D 3/12* | (2006.01) | |
| *C11D 3/22* | (2006.01) | |
| *A61K 8/26* | (2006.01) | |
| *A61K 8/60* | (2006.01) | |
| *A61Q 19/00* | (2006.01) | |
| *C11D 3/20* | (2006.01) | |
| *C11D 3/37* | (2006.01) | |
| *C11D 3/50* | (2006.01) | |

(52) U.S. Cl.
CPC ............ *C11D 17/0034* (2013.01); *A61K 8/26* (2013.01); *A61K 8/60* (2013.01); *A61Q 19/00* (2013.01); *C11D 3/001* (2013.01); *C11D 3/046* (2013.01); *C11D 3/126* (2013.01); *C11D 3/2075* (2013.01); *C11D 3/221* (2013.01); *C11D 3/227* (2013.01); *C11D 3/373* (2013.01); *C11D 3/3742* (2013.01); *C11D 3/3769* (2013.01); *C11D 3/3776* (2013.01); *C11D 3/505* (2013.01); *A61K 2800/31* (2013.01)

(58) Field of Classification Search
USPC ................ 510/445, 349, 441, 442, 485, 507
See application file for complete search history.

(56) References Cited

U.S. PATENT DOCUMENTS

| | | | | |
|---|---|---|---|---|
| 4,375,416 A | * | 3/1983 | Crisp et al. ................... | 510/332 |
| 4,539,135 A | | 9/1985 | Ramachandran et al. | |
| 4,675,124 A | * | 6/1987 | Seiter ....................... | C11D 1/83 |
| | | | | 427/220 |
| 5,407,594 A | * | 4/1995 | Fry et al. ...................... | 510/439 |
| 5,656,584 A | * | 8/1997 | Angell ................... | C11D 3/222 |
| | | | | 510/101 |
| 6,114,289 A | * | 9/2000 | Capeci et al. ................ | 510/108 |
| 6,531,433 B1 | * | 3/2003 | Kobayashi et al. .......... | 510/130 |
| 6,846,795 B2 | * | 1/2005 | Lant et al. .................... | 510/446 |
| 7,285,426 B2 | | 10/2007 | Bohannon | |
| 7,655,612 B2 | * | 2/2010 | Zak ........................ | C11D 1/662 |
| | | | | 510/470 |
| 2003/0036489 A1 | * | 2/2003 | Liu et al. ....................... | 510/100 |
| 2003/0166489 A1 | * | 9/2003 | Van Asten et al. ........... | 510/440 |
| 2005/0153863 A1 | * | 7/2005 | Corominas ................... | 510/446 |
| 2009/0042766 A1 | | 2/2009 | Mayer et al. | |
| 2009/0082244 A1 | | 3/2009 | Mayer et al. | |

FOREIGN PATENT DOCUMENTS

| | | |
|---|---|---|
| EP | 0 165 056 A2 | 12/1985 |
| EP | 0 215 637 A2 | 3/1987 |
| EP | 0 483 411 B1 | 5/1992 |
| EP | 1 561 802 B1 | 8/2005 |
| GB | 2 331 305 A | 5/1999 |
| WO | WO 99/57258 | 11/1999 |
| WO | WO 00/17298 A1 | 3/2000 |
| WO | WO 03/055966 A1 | 7/2003 |
| WO | WO 2005/005591 A1 | 1/2005 |
| WO | WO 2006/053598 A1 | 5/2006 |
| WO | WO 2007/113069 A1 | 10/2007 |
| WO | WO 2007/115872 A1 | 10/2007 |

OTHER PUBLICATIONS

International Search Report of PCT/EP2007/060812, dated Feb. 4, 2008.
Wikipedia, "Dextrin," http://en.wikipedia.org/wiki/Dextrin, Oct. 19, 2010.
Wikipedia, "Glucose," http://en.wikipedia.org/wiki/Glucose, Oct. 19, 2010.
Wikipedia, "Maltodextrin," http://en.wikipedia.org/wiki/Maltodextrin, Oct. 19, 2010.
"Mixing," McGraw-Hill Dictionary of Scientific and Technical Terms, 1994, p. 1281, fifth edition, McGraw-Hill, Inc., USA, ISBN 0-07-042333-4.
"Mixture," McGraw-Hill Concise Encyclopedia of Science & Technology, 1984, p. 1093, McGraw-Hill, Inc, USA, ISBN 0-07-045482-5.
"Mixture," Webster's Ninth New Collegiate Dictionary, 1991, p. 761, Merriam-Webster Inc, Springfield, MA, USA, ISBN 0-87779-508.8.

* cited by examiner

*Primary Examiner* — Ling Siu Choi
*Assistant Examiner* — Thuy-Ai N Nguyen
(74) *Attorney, Agent, or Firm* — RatnerPrestia

(57) ABSTRACT

Solid textile- and/or skin-care compositions encompassing a water-soluble particle and a water-insoluble particle that contains a water-insoluble carrier and a textile- and/or skin-care compound. Also, textile-softening washing detergents or cleaning agents encompassing the textile- and/or skin-care composition.

19 Claims, No Drawings

SOLID TEXTILE CARE AND/OR SKINCARE COMPOSITION

CROSS-REFERENCE TO RELATED APPLICATIONS

This application is a continuation under 35 U.S.C. §§ 120 and 365(c) of International Application PCT/EP2007/060812, filed on Oct. 11, 2007. This application also claims priority under 35 U.S.C. § 119 of DE 10 2006 054 436.6, filed on Nov. 16, 2006. The disclosures of PCT/EP2007/060812 and DE 10 2006 054 436.6 are incorporated herein by reference in their entirety.

BACKGROUND OF THE INVENTION

The invention relates to a solid textile- and/or skin-care composition and to the use and manufacture thereof. In addition, the invention relates to a washing detergent or cleaning agent containing the solid textile- and/or skin-care composition.

Repeated washing often causes textiles to become hard and lose their softness. In order to restore softness and flexibility to textiles, in order to impart a pleasant scent to them, and/or in order to improve their anti-static properties, the textiles are treated with a fabric softener in a subsequent rinsing process after the actual washing and cleaning process.

Most fabric softeners on the market are aqueous formulations that contain as the principal active constituent a cationic textile-softening compound that comprises one or more long-chain alkyl groups in one molecule. Widely used cationic textile-softening compounds encompass, for example, methyl-N-(2-hydroxyethyl)-N,N-di(tallowacyloxyethyl)ammonium compounds, or N,N-dimethyl-N,N-di(tallowacyloxyethyl)ammonium compounds.

Because of the cationic textile-softening compounds, these conventional fabric softener formulations cannot be used simultaneously with the washing detergent or cleaning agent in the actual washing or cleaning process, since the cationic textile-softening compounds interact undesirably with the anionic surfactants of the washing detergent or cleaning agent. An additional rinsing operation is therefore necessary, but this is time- and energy-intensive.

A further disadvantage is that conventional fabric softeners do not prevent the deposition of lime residues onto the laundry during the rinsing operation. In addition, the conventional fabric softeners often leave behind an unattractive deposit in the bleach dispenser of the washing machine.

DETAILED DESCRIPTION OF THE INVENTION

It is therefore an object of the present invention to make available a textile- and/or skin-care composition that can be used in the main washing cycle together with washing detergents or cleaning agents.

This object is achieved by a solid textile- and/or skin-care composition encompassing a water-soluble particle and a water-insoluble particle that contains a water-insoluble carrier and a textile- and/or skin-care compound.

A textile- and/or skin-care composition of this kind can be used in the main washing cycle of an automatic washing or cleaning process. The textile- and/or skin-care composition can, for example, be introduced together with the washing detergent or cleaning agent into the drum or into the bleach dispenser of a washing machine. This has the advantage that an additional rinse cycle is not necessary, and that unattractive deposits do not occur in the bleach dispenser.

It is furthermore advantageous that the textile- and/or skin-care compound is transported directly to the laundry already at the beginning of the washing process, and can thus achieve its full potential.

Because consumers tend to over-dispense especially in the case of concentrated products, and because over-dispensing can result not only in unattractive deposits on the textiles but also in frustration on the part of the consumer regarding the yield of a product, the textile- and/or skin-care composition contains water-insoluble particles as fillers.

It is preferred that the water-soluble particle contain a compound selected from the group consisting of inorganic alkali metal salts, organic alkali metal salts, inorganic alkaline earth metal salts, organic alkaline earth metal salts, organic acids, carbohydrates, silicates, and mixtures thereof.

These materials are not only inexpensive but also dissolve very well in water. Furthermore these materials have a neutral odor.

It is particularly preferred that the water-soluble particle encompass a carbohydrate, and be selected from the group consisting of dextrose, fructose, galactose, isoglucose, glucose, sucrose, raffinose, and mixtures thereof.

The use of a water-soluble particle that comprises, or at least predominantly comprises, carbohydrates, obviates the problem of corrosion in the washing machine, which can occur particularly when using inorganic salts as a water-soluble particle.

It is advantageous that the solid textile- and/or skin-care composition contains 10 to 90 wt %, preferably 40 to 60 wt %, and very particularly preferably 45 to 55 wt %, water-soluble particles.

It is further preferred that the water-insoluble carrier be a textile-softening clay, in particular a bentonite.

Textile-softening clays are particularly suitable as carriers for other compounds because clays can easily absorb or adsorb them, and impart softness to textiles treated therewith. They also have a water-softening effect, so that lime deposits on the laundry are additionally prevented when they are used.

It is particularly preferred that the textile- and/or skin-care compound be selected from the group consisting of textile-softening compounds, fluorescing agents, anti-redeposition agents, optical brighteners, graying inhibitors, shrinkage preventers, wrinkle protection agents, color transfer inhibitors, antimicrobial active substances, germicides, fungicides, antioxidants, antistatic agents, ironing adjuvants, UV absorbers, repellent agents, impregnation agents, skin-care compounds, perfumes, and mixtures thereof.

An advantageous effect is imparted to the textiles treated with the textile- and/or skin-care composition according to the present invention by the addition of one or more of these textile- and/or skin-care compounds, or damaging or negative effects on the textiles that can occur during cleaning and/or conditioning and/or wearing, such as e.g. fading, graying, etc., are reduced.

It is very particularly preferred that the water-insoluble particle contain, as a textile-softening compound, a textile-softening compound selected from the group consisting of polysiloxanes, cationic polymers, and mixtures thereof.

A particularly good textile-softening effect can be imparted to the textile- and/or skin-care composition as a result of the addition of a textile-softening polymer, in particular a polysiloxane, a cationic polymer, or a mixture thereof.

In a further particularly preferred embodiment, the water-insoluble particle contains a perfume as a textile- and/or skin-care compound. It is particularly preferred in this context that the quantity of perfume be 0.1 to 20 wt %, preferably 1 to 10 wt %, and particularly preferably 2 to 7 wt %.

Textile- and/or skin-care compositions are usually also intended to impart a pleasant and long-lasting scent to the laundry, and for that reason preferably contain a perfume. The perfume impression of the laundry can be intensified in this context by means of polysiloxanes and/or cationic polymers that may be present in the textile- and/or skin-care composition. A further advantage of the textile- and/or skin-care composition according to the present invention that is used in the main washing cycle is that the perfume is transported directly to the laundry already at the beginning of the washing and cleaning process, and can thus achieve its full potential.

With conventional liquid fabric softener compositions having quaternary ammonium compounds as a textile-softening compound, at higher perfume concentrations (>0.4 wt % perfume for regular fabric softener compositions and ≥1 wt % for concentrated fabric softener compositions) a problem also occurs with the stability of the composition. With the textile- and/or skin-care compositions according to the present invention, larger quantities of perfume (≥1 wt %) can be incorporated without difficulty.

It is further preferred that the water-insoluble particle additionally contain ingredients selected from the group consisting of dyes, fillers, luster agents, and mixtures thereof.

It is particularly preferred that the water-soluble particle and/or the water-insoluble particle each have a particle size in the range from 0.6 to 30 mm, in particular 0.8 to 20 mm, and particularly preferably 1 to 10 mm.

Textile- and/or skin-care compositions having particle sizes in these ranges can be dispensed in particularly effective and controlled fashion.

The invention also relates to the use of a solid textile- and/or skin-care composition according to the present invention for conditioning textile fabrics.

The invention further relates to a method for manufacturing a solid textile- and/or skin-care composition, in which method a water-soluble particle and a water-insoluble particle, which contains a water-insoluble carrier and a textile- and/or skin-care compound, are mixed.

The invention moreover relates to a washing detergent or washing agent encompassing a solid textile- and/or skin-care composition according to the present invention.

By introducing the textile- and/or skin-care composition according to the present invention into a washing detergent or cleaning agent, washing detergents or cleaning agents having different textile- and/or skin-care effects can be obtained easily and quickly, since only the composition of the textile- and/or skin-care composition needs to be modified. In addition, for example in the context of addition of a perfume to the textile- and/or skin-care composition, it is not necessary to perfume the washing detergent or cleaning agent and the textile- and/or skin-care composition, but instead only one of the two agents, by preference the textile- and/or skin-care composition. This not only results in lower costs and an elimination of scent impression overlay when two differently perfumed products are used, but is also advantageous for consumers with sensitive skin and/or allergies.

The invention also relates to a method for manufacturing a washing detergent or cleaning agent encompassing a solid textile- and/or skin-care composition according to the present invention, in which method a solid washing detergent or cleaning agent is mixed with a solid textile- and/or skin-care composition according to the present invention.

Another subject of the invention is the use of a washing detergent or cleaning agent, encompassing a textile- and/or skin-care composition according to the present invention, for cleaning and conditioning textile fabrics.

The invention will be explained below in more detail, with reference inter alia to examples.

The solid textile- and/or skin-care composition contains, as essential constituents, a water-soluble particle and a water-insoluble particle. The water-insoluble particle encompasses a water-insoluble carrier and a textile- and/or skin-care compound.

"Water-insoluble particle" means in this context that the particle is not entirely water-soluble, and comprises a certain proportion, by preference at least 10 wt %, of water-insoluble compounds.

The water-insoluble carrier of the water-insoluble particle is by preference a textile-softening clay such as, for example, a smectite clay. Preferred smectite clays are beidellite clays, hectorite clays, laponite clays, montmorillonite clays, nontronite clays, saponite clays, sauconite clays, and mixtures thereof. Montmorillonite clays are the preferred softening clays. Bentonites contain principally montmorillonites, and can serve as a preferred source for the textile-softening clay.

Suitable bentonites are marketed, for example, under the designation Laundrosil® by the Süd-Chemie company, or under the designation Detercal by the Laviosa company.

Particularly preferably, the water-insoluble carrier is a granulated bentonite.

The quantity of water-insoluble carrier in the water-insoluble particle is between 10 and 90 wt %, and is preferably 40 to 50 wt %.

In addition to the water-insoluble carrier, the water-insoluble particle contains a textile- and/or skin-care compound. The latter is preferably selected from the group consisting of textile-softening compounds, fluorescing agents, anti-redeposition agents, optical brighteners, graying inhibitors, shrinkage preventers, wrinkle protection agents, color transfer inhibitors, antimicrobial active substances, germicides, fungicides, antioxidants, antistatic agents, ironing adjuvants, UV absorbers, repellent agents, impregnation agents, skin-care compounds, perfume, and mixtures thereof.

It is preferred in this context that the textile- and/or skin-care composition contain as a textile-softening compound a textile-softening polymer, in particular a polysiloxane and/or a cationic polymer.

A polysiloxane that is usable in preferred fashion comprises at least the following structural unit:

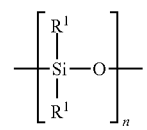

a)

in which
$R^1$=(mutually independently) $C_1$ to $C_{30}$ alkyl, by preference $C_1$ to $C_4$ alkyl, in particular methyl or ethyl,
n=1 to 5000, by preference 10 to 2500, in particular 100 to 1500.

It may be preferred for the polysiloxane also to comprise, additionally, the following structural unit:

$$\left[\begin{array}{c} R^1 \\ | \\ Si-O \\ | \\ Y \\ | \\ R^3 \diagdown N \diagup R^2 \end{array}\right]_x \quad b)$$

in which
R$^1$=C$_1$ to C$_{30}$ alkyl, by preference C$_1$ to C$_4$ alkyl, in particular methyl or ethyl,
Y=optionally substituted, linear or branched C$_1$ to C$_{20}$ alkylene, by preference —(CH$_2$)$_m$— where m=1 to 16, by preference 1 to 8, in particular 2 to 4, especially 3,
R$^2$, R$^3$=(mutually independently) H or optionally substituted, linear or branched C$_1$ to C$_{30}$ alkyl, by preference C$_1$ to C$_{30}$ alkyl substituted with amino groups, particularly preferably —(CH$_2$)$_b$—NH$_2$ where b=1 to 10, extremely preferably b=2,
x=1 to 5000, by preference 10 to 2500, in particular 100 to 1500.

If the polysiloxane comprises only structural unit a) in which R$^1$=methyl, this is a polydimethylsiloxane. Polydimethylsiloxanes are known as efficient textile-care compounds.

Suitable polydimethylsiloxanes encompass DC-200 (from Dow Corning), Baysilone® M 50, Baysilone® M 100, Baysilone® M 350, Baysilone® M 500, Baysilone® M 1000, Baysilone® M 1500, Baysilone® M 2000, or Baysilone® M 5000 (all from GE Bayer Silicones).

It may also be preferred, however, for the polysiloxane to contain structural units a) and b). A particularly preferred polysiloxane exhibits the following structure:

(CH$_3$)$_3$Si—[O—Si(CH$_3$)2]$_n$—[O—Si(CH$_3$)
{(CH$_2$)$_3$—NH—(CH$_2$)$_2$—NH$_2$}]$_x$—OSi(CH$_3$)$_3$, the sum n+x being a number between 2 and 10,000.

Suitable polysiloxanes having structural units a) and b) are obtainable commercially, for example, under the trade names DC2-8663, DC2-8035, DC2-8203, DC05-7022, or DC2-8566 (all from Dow Corning). Also suitable according to the present invention are, for example, the commercially obtainable products Dow Corning® 7224, Dow Corning® 929 Cationic Emulsion, or Formasil 410 (GE Silicones).

Suitable cationic polymers encompass, in particular, those that are described in the "CTFA International Cosmetic Ingredient Dictionary," fourth edition, J. M. Nikitakis et al., editors, published by the Cosmetic, Toiletry, and Fragrance Association, 1991, and grouped under the general designation "Polyquaternium." Some suitable polyquaternium compounds are described in more detail below.

POLYQUATERNIUM-1 (CAS no. 68518-54-7)
Definition: {(HOCH$_2$CH$_2$)$_3$N$^+$—CH$_2$CH=CHCH$_2$—[N$^+$(CH$_3$)$_2$—CH$_2$CH=CHCH$_2$]$_x$—N$^+$(CH$_2$CH$_2$OH)$_3$}[Cl]$_{x+2}$ POLYQUATERNIUM-2 (CAS no. 63451-27-4)
Definition: [—N(CH$_3$)$_2$—CH$_2$CH$_2$CH$_2$—NH—C(O)—NH—CH$_2$CH$_2$CH$_2$—N(CH$_3$)$_2$—CH$_2$CH$_2$OCH$_2$CH$_2$—]$^{2+}$(Cl$^-$)$_2$
Obtainable, for example, as Mirapol® A-15 (from Rhodia).

POLYQUATERNIUM-3
Definition: Copolymer of acrylamide and trimethylammonium ethyl methacrylate methosulfate.

POLYQUATERNIUM-4 (CAS no. 92183-41-0)
Definition: Copolymer of hydroxyethyl cellulose and diallyldimethylammonium chloride. Obtainable, for example, as Celquate® H 100 or Celquate® L200 (from National Starch).

POLYQUATERNIUM-5 (CAS no. 26006-22-4)
Definition: Copolymer of acrylamide and β-methacryloyloxyethyltrimethylammonium methosulfate. Obtainable, for example, as Nalco 7113 (from Nalco) or Reten® 210, Reten® 220, Reten® 230, Reten® 240, Reten® 1104, Reten® 1105, or Reten® 1106 (all from Hercules).

POLYQUATERNIUM-6 (CAS no. 26062-79-3) Definition: Polymer of dimethyldiallylammonium chloride. Obtainable, for example, as Merquat® 100 (from Ondeo-Nalco).

POLYQUATERNIUM-7 (CAS no. 26590-05-6)
Definition: Polymeric quaternary ammonium salt made up of acrylamide and dimethyldiallylammonium chloride monomers. Obtainable, for example, as Merquat® 550 or Merquat® S (from Ondeo-Nalco).

POLYQUATERNIUM-8
Definition: Polymeric quaternary ammonium salt of methyl- and stearyldimethylaminoethyl methacrylate that has been quaternized with dimethyl sulfate.

POLYQUATERNIUM-9
Definition: Polymeric quaternary ammonium salt of polydimethylaminoethyl methacrylate that has been quaternized with methyl bromide.

POLYQUATERNIUM-10 (CAS nos. 53568-66-4; 55353-19-0; 54351-50-7; 81859-24-7; 68610-92-4; 81859-24-7)
Definition: Polymeric quaternary ammonium salt of hydroxyethyl cellulose that has been reacted with a trimethylammonium-substituted epoxide. Obtainable, for example, as Celquat® SC-240 (from National Starch), UCARE® Polymer JR-125, UCARE® Polymer JR-400, UCARE® Polymer JR-30M, UCARE® Polymer LR 400, UCARE® Polymer LR 30M, Ucare® Polymer SR-10 (all from Amerchol).

POLYQUATERNIUM-11 (CAS no. 53633-54-8)
Definition: Quaternary ammonium polymer that is formed by reacting diethyl sulfate with the copolymer of vinylpyrrolidone and dimethylaminoethyl methacrylate. Obtainable, for example, as Luviquat® PQ 11 PN (from BASF), Gafquat® 734, Gafquat® 755, or Gafquat® 755N (from GAF).

POLYQUATERNIUM-12 (CAS no. 68877-50-9)
Definition: Quaternary ammonium polymer salt obtainable by reacting ethyl methacrylate/abietyl methacrylate/diethylaminoethyl methacrylate copolymer with dimethyl sulfate.

POLYQUATERNIUM-13 (CAS no. 68877-47-4)
Definition: Polymeric quaternary ammonium salt obtainable by reacting ethyl methacrylate/oleyl methacrylate/diethylaminoethyl methacrylate copolymer with dimethyl sulfate.

POLYQUATERNIUM-14 (CAS no. 27103-90-8)
Definition: Polymeric quaternary ammonium salt having the formula —{—CH$_2$—C—(CH$_3$)—[C(O)O—CH$_2$CH$_2$—N(CH$_3$)$_3$—]}$_x^+$ [CH$_3$SO$_4$]$^-$$_x$.

POLYQUATERNIUM-15 (CAS no. 35429-19-7)
Definition: Copolymer of acrylamide and β-methacryloyloxyethyltrimethylammonium chloride.

POLYQUATERNIUM-16 (CAS no. 95144-24-4)
Definition: Polymeric quaternary ammonium salt formed from methylvinylimidazolium chloride and vinylpyrrolidone. Obtainable, for example, as Luviquat® FC 370, Luviquat® Style, Luviquat® FC 550, or Luviquat® Excellence (all from BASF).

POLYQUATERNIUM-17 (CAS no. 90624-75-2)
Definition: Polymeric quaternary ammonium salt obtainable by reacting adipic acid and dimethylaminopropylamine with dichloroethyl ether. Obtainable, for example, as Mirapol® AD-1 (from Rhodia).

POLYQUATERNIUM-18
Definition: Polymeric quaternary ammonium salt obtainable by reacting azelaic acid and dimethylaminopropylamine with dichloroethyl ether. Obtainable, for example, as Mirapol® AZ-1 (from Rhodia).

POLYQUATERNIUM-19
Definition: Polymeric quaternary ammonium salt obtainable by reacting polyvinyl alcohol with 2,3-epoxypropylamine.

POLYQUATERNIUM-20
Definition: Polymeric quaternary ammonium salt obtainable by reacting polyvinyloctadecyl ether with 2,3-epoxypropylamine.

POLYQUATERNIUM-21 (CAS no. 102523-94-4)
Definition: Polysiloxane/polydimethyldiallylammonium acetate copolymer. Obtainable, for example, as Abil® B 9905 (from Goldschmidt-Degussa).

POLYQUATERNIUM-22 (CAS no. 53694-17-0)
Definition: Dimethyldiallylammonium chloride/acrylic acid copolymer. Obtainable, for example, as Merquat® 280 (from Ondeo-Nalco).

POLYQUATERNIUM-24 (CAS no. 107987-23-5)
Definition: Polymeric quaternary ammonium salt resulting from the reaction of hydroxyethyl cellulose with a lauryldimethylammonium-substituted epoxide. Obtainable, for example, as Quatrisoft.

POLYQUATERNIUM-27
Definition: Block copolymer resulting from the reaction of Polyquaternium-2 with Polyquaternium-17.

POLYQUATERNIUM-28 (CAS no. 131954-48-8)
Definition: Vinylpyrrolidone/methacrylamidopropyltrimethylammonium chloride copolymer. Obtainable, for example, as Gafquat® HS-100 (from GAF).

POLYQUATERNIUM-29
Definition: Chitosan that has been reacted with propylene oxide and quaternized with epichlorohydrin.

POLYQUATERNIUM-30
Definition: Polymeric quaternary ammonium salt having the formula $-[CH_2C(CH_3)(C(O)OCH_3)]_x-[CH_2C(CH_3)(C(O)OCH_2CH_2N^+(CH_3)_2CH_2COO^-)]_y-$.

POLYQUATERNIUM-31 (CAS no. 136505-02-7)
POLYQUATERNIUM-32 (CAS no. 35429-19-7)
Definition: Polymer of N,N,N-trimethyl-2-[(2-methyl-1-oxo-2-propenyl)oxy]ethanaminium chloride with 2-propenamide.

POLYQUATERNIUM-37 (CAS no. 26161-33-1)
Definition: Homopolymer of methacryloyltrimethyl chloride. Obtainable, for example, as Synthalen® CR (from 3V Sigma).

POLYQUATERNIUM-44 (CAS no. 150595-70-5)
Definition: Quaternized ammonium salt of the copolymer of vinylpyrrolidone and quaternized imidazoline. Obtainable, for example, as Luviquat® Ultracare (from BASF).

POLYQUATERNIUM-68 (CAS no. 827346-45-2)
Definition: Quaternized copolymer of vinylpyrrolidone, methacrylamide, vinylimidazole, and quaternized vinylimidazole. Obtainable, for example, as Luviquat® Supreme (from BASF).

The cationic polymers do not necessarily have only a textile-softening effect, but can additionally exhibit a further textile- and/or skin-care effect.

A "skin-care compound" is understood as a compound or mixture of compounds that, upon contact between a textile and the solid textile- and/or skin-care composition, absorbs onto the textile and, upon contact between the textile and skin, imparts to the skin an advantage compared with a textile that was not treated with the textile- and/or skin-care composition according to the present invention. This advantage can encompass, for example, transfer of the skin-care compound from the textile onto the skin, a decreased transfer of water from the skin onto the textile, or decreased friction on the skin surface as a result of the textile.

A skin-care compound is by preference hydrophobic, can be liquid or solid, and must be compatible with the other ingredients of the solid textile- and/or skin-care composition. The skin-care compound can encompass, for example:
a) waxes such as carnauba, spermaceti, beeswax, lanolin, derivatives thereof and mixtures thereof;
b) hydrophobic plant extracts, for example vegetable oils such as avocado oil, olive oil, palm oil, palm kernel oil, rapeseed oil, linseed oil, soy oil, peanut oil, coriander oil, castor oil, poppy-seed oil, cocoa oil, coconut oil, pumpkin seed oil, wheat germ oil, sesame oil, sunflower oil, almond oil, macadamia nut oil, apricot kernel oil, hazelnut oil, jojoba oil, canola oil, and mixtures thereof, aloe vera or chamomile;
c) higher fatty acids such as lauric acid, myristic acid, palmitic acid, stearic acid, behenic acid, oleic acid, linoleic acid, linolenic acid, isostearic acid, or polyunsaturated fatty acids;
d) higher fatty alcohols such as lauryl alcohol, cetyl alcohol, stearyl alcohol, oleyl alcohol, behenyl alcohol, or 2-hexadecanol;
e) esters such as cetyl octanoate, lauryl lactate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate, or alkyl tartrate;
f) hydrocarbons such as paraffins, mineral oils, squalane, or squalene;
g) lipids;
h) vitamins such as vitamin A, C, or E, or vitamin alkyl esters;
i) phospholipids;
j) sun protectants such as octyl methoxycinnamate and butylmethoxybenzoylmethane;
k) silicone oils, such as linear or cyclic polydimethylsiloxanes, amino-, alkyl-, alkylaryl-, or aryl-substituted silicone oils; and
l) mixtures thereof.

The water-insoluble particle can furthermore contain a perfume as a textile- and/or skin-care compound. It is in fact particularly preferred that the water-insoluble particle contain a perfume.

Individual odorant compounds, e.g. the synthetic products of the ester, ether, aldehyde, ketone, alcohol, and hydrocarbon types, can be used as perfume oils or fragrances. It is preferable, however, to use mixtures of different odorants that together produce an appealing fragrance note. Perfume oils of this kind can also contain natural odorant mixtures such as those accessible from plant sources.

The quantity of perfume in the textile- and/or skin-care composition is by preference between 0.1 and 20 wt %, particularly preferably between 1 and 10 wt %, and very particularly preferably between 2 and 7 wt %.

Further suitable textile-care compounds preferably encompass fluorescing agents, anti-redeposition agents, optical brighteners, graying inhibitors, shrinkage preventers, wrinkle protection agents, color transfer inhibitors, antimicrobial active substances, germicides, fungicides, antioxidants, antistatic agents, ironing adjuvants, UV absorbers, repellent agents, and/or impregnation agents. Concrete examples of these textile-care compounds may be found in the description of the washing detergent or cleaning agent according to the present invention, and can also be used in the solid textile- and/or skin-care composition.

The solid textile- and/or skin-care composition can also contain mixtures of the aforesaid compounds.

The quantity of textile- and/or skin-care compound in the textile- and/or skin-care composition is 0.1 to 20 wt %.

A further essential constituent of the solid textile- and/or skin-care composition is the water-soluble particle. The latter preferably encompasses inorganic alkali metal salts such as, for example, sodium chloride, potassium chloride, sodium sulfate, sodium carbonate, potassium sulfate, potassium carbonate, sodium hydrogencarbonate, potassium hydrogencarbonate, or mixtures thereof, organic alkali metal salts such as, for example, sodium acetate, potassium acetate, sodium citrate, sodium tartrate, or potassium sodium tartrate, inorganic alkaline earth metal salts such as, for example, calcium chloride or magnesium chloride, organic alkaline earth metal salts such as, for example, calcium lactate, carbohydrates, organic acids such as, for example, citric acid or tartaric acid, silicates such as, for example, water glass, sodium silicate, or potassium silicate, and mixtures thereof. The water-soluble carrier can also, in particular, encompass a carbohydrate, which for example is selected from the group consisting of dextrose, fructose, galactose, isoglucose, glucose, sucrose, raffinose, and mixtures thereof. The carbohydrate used can be, for example, sugar candy, tea sugar, crystal sugar, or pearl sugar. Because of its extraordinary aesthetic and acoustic properties, it is preferred to use a sugar as a water-soluble particle or as a predominant constituent of a water-soluble particle.

The water-soluble particle can also contain mixtures of the aforesaid materials. The water-soluble particle can, for example, also be made up of a water-soluble carrier particle and further compounds.

It is preferred that the water-soluble particle and the water-insoluble particle each have particle sizes in the range from 0.6 to 30 mm, in particular 0.8 to 20 mm, and particularly preferably 1 to 10 mm. Particularly preferably, the water-soluble particle encompasses sucrose crystals having a particle size from 1 to 2 mm.

It is particularly preferred that the particle sizes of the water-soluble particles and of the water-insoluble particles be in a similar range, i.e. on the same order of magnitude, in order to prevent demixing of the particles.

Suitable methods for determining the particle size of particles (e.g. powders, granulates, or agglomerates) are sufficiently known to one skilled in the art. In the context of this invention, the particle sizes of the water-soluble particle, the water-soluble carrier particle, the water-insoluble particle, and/or the water-insoluble carrier particle were determined by means of sieve analyses.

The water-soluble particle and the water-insoluble particle can each optionally contain further ingredients.

In order to improve the aesthetic impression of the textile- and/or skin-care composition, the particles can be colored with suitable dyes. Preferred dyes, the selection of which will present no difficulty whatsoever to one skilled in the art, possess excellent shelf stability and insensitivity to the other ingredients of the washing detergents or cleaning agents and to light, and no pronounced substantivity with respect to textile fibers, in order not to color them.

The water-soluble particle and/or the water-insoluble particle can furthermore contain a filler, such as silica. The quantity of filler in the particles can in each case be between 0.1 and 10 wt %, and is preferably 1 to 5 wt %.

In order to increase luster, the particles, and in particular the water-insoluble particle, can each also contain a luster agent. Examples of suitable luster agents are ethylene glycol mono- and distearate (e.g. Cutina® AGS of Cognis), as well as PEG-3 distearate.

For the manufacture of the textile- and/or skin-care composition, firstly the two particles are manufactured or made available in separate processes. In the case of the water-soluble particles, the process for making available may involve simply acquiring the water-soluble compound having the desired particle size, and coloring the compounds.

For the manufacture of the water-insoluble particles, the water-insoluble carrier particles are treated/impregnated, for example, by spraying with a liquid that contains the textile- and/or skin-care compound.

The textile- and/or skin-care composition is suitable in particular for conditioning textile fabrics, and for that purpose is brought into contact with the textile fabrics, together with a conventional washing detergent or cleaning agent, in the (main) washing cycle of a conventional laundering and cleaning process.

The textile- and/or skin-care composition can be introduced into a washing detergent or cleaning agent.

For that purpose, a solid washing detergent or cleaning agent is mixed with 0.1 to 20 wt %, by preference 1 to 10 wt %, based on the entire washing detergent or cleaning agent according to the present invention, of the textile- and/or skin-care composition according to the present invention.

The washing detergents or cleaning agents according to the present invention contain surfactant(s) in addition to the textile- and/or skin-care composition; anionic, nonionic, zwitterionic, and/or amphoteric surfactants can be used. Mixtures of anionic and nonionic surfactants are preferred from the standpoint of applications engineering. The total surfactant content of a washing detergent is by preference below 40 wt % and particularly preferably below 35 wt %, based on the entire washing detergent.

The nonionic surfactants used are preferably alkoxylated, advantageously ethoxylated, in particular primary alcohols having by preference 8 to 18 carbon atoms and an average of 1 to 12 mol ethylene oxide (EO) per mol of alcohol, in which the alcohol radical can be linear or preferably methyl-branched in the 2-position, or can contain mixed linear and methyl-branched radicals, such as those that are usually present in oxo alcohol radicals. Particularly preferred, however, are alcohol ethoxylates having linear radicals made up of alcohols of natural origin having 12 to 18 carbon atoms, e.g. from coconut, palm, tallow, or oleyl alcohol, and an average of 2 to 8 EO per mol of alcohol. The preferred ethoxylated alcohols include, for example, $C_{12-14}$ alcohols having 3 EO, 4 EO, or 7 EO, $C_{9-11}$ alcohol having 7 EO, $C_{13-15}$ alcohols having 3 EO, 5 EO, 7 EO, or 8 EO, $C_{12-18}$ alcohols having 3 EO, 5 EO, or 7 EO, and mixtures thereof, such as mixtures of $C_{12-14}$ alcohol having 3 EO and $C_{12-18}$ alcohol having 7 EO. The degrees of ethoxylation indicated represent statistical averages, which can correspond to an integer or a fraction for a specific product. Preferred alcohol ethoxylates exhibit a restricted distribution of homologs (narrow range ethoxylates, NRE). In addition to these nonionic surfactants, fatty alcohols having more than 12 EO can also be used. Examples of these are tallow fatty alcohol having 14 EO, 25 EO, 30 EO, or 40 EO. Nonionic surfactants that contain EO and PO groups together in the molecule are also usable according to the present invention. Block copolymers having EO-PO block units or PO-EO block units, but also EO-PO-EO copolymers or PO-EO-PO copolymers, can be used in this context. Also usable, of course, are mixed alkoxylated nonionic surfactants in which EO and PO units are distributed statistically rather than in block fashion. Such products are obtainable by the simultaneous action of ethylene oxide and propylene oxide on fatty alcohols.

Also usable as further nonionic surfactants are alkyl glycosides of the general formula $RO(G)_x$, in which R denotes a primary straight-chain or methyl-branched (in particular methyl-branched in the 2-position) aliphatic radical having 8 to 22, by preference 12 to 18 carbon atoms; and G is the symbol denoting a glycose unit having 5 or 6 carbon atoms, preferably glucose. The degree of oligomerization x, which indicates the distribution of monoglycosides and oligoglycosides, is any number between 1 and 10; by preference, x is between 1.2 and 1.4. Alkyl glycosides are known mild surfactants.

A further class of nonionic surfactants used in preferred fashion, which are used either as the only nonionic surfactant or in combination with other nonionic surfactants, are alkoxylated, preferably ethoxylated or ethoxylated and propoxylated, fatty acid alkyl esters, by preference having 1 to 4 carbon atoms in the alkyl chain, in particular fatty acid methyl esters.

Nonionic surfactants of the amine oxide type, for example N-cocalkyl-N,N-dimethylamine oxide and N-tallowalkyl-N,N-dihydroxyethylamine oxide, and the fatty acid alkanolamides, can also be suitable. The quantity of these nonionic surfactants is by preference no more than that of the ethoxylated fatty alcohols, in particular no more than half thereof.

Further suitable surfactants are polyhydroxy fatty acid amides of formula (VII)

(VII)

in which RCO denotes an aliphatic acyl radical having 6 to 22 carbon atoms; $R^1$ denotes hydrogen, an alkyl or hydroxyalkyl radical having 1 to 4 carbon atoms; and [Z] denotes a linear or branched polyhydroxyalkyl radical having 3 to 10 carbon atoms and 3 to 10 hydroxyl groups. The polyhydroxy fatty acid amides are known substances that can usually be obtained by reductive amination of a reducing sugar with ammonia, an alkylamine, or an alkanolamine, and subsequent acylation with a fatty acid, a fatty acid alkyl ester, or a fatty acid chloride.

Also belonging to the group of the polyhydroxy fatty acid amides are compounds of formula (VIII)

(VIII)

in which R denotes a linear or branched alkyl or alkenyl radical having 7 to 12 carbon atoms; $R^1$ denotes a linear, branched, or cyclic alkyl radical or an aryl radical having 2 to 8 carbon atoms; and $R^2$ denotes a linear, branched, or cyclic alkyl radical or an aryl radical or an oxyalkyl radical having 1 to 8 carbon atoms, $C_{1-4}$ alkyl or phenyl radicals being preferred; and [Z] denotes a linear polyhydroxyalkyl radical whose alkyl chain is substituted with at least two hydroxyl groups, or alkoxylated, preferably ethoxylated or propoxylated, derivatives of that radical.

[Z] is preferably obtained by reductive amination of a reducing sugar, for example glucose, fructose, maltose, lactose, galactose, mannose, or xylose. The N-alkoxy- or N-aryloxy-substituted compounds can then be converted into the desired polyhydroxy fatty acid amides by reaction with fatty acid methyl esters in the presence of an alkoxide as catalyst.

The concentration of nonionic surfactants in the washing detergents or cleaning agents is preferably 5 to 30 wt %, by preference 7 to 20 wt %, and in particular 9 to 15 wt %, based in each case on the entire washing detergent or cleaning agent.

Anionic surfactants that can be used are, for example, those of the sulfonate and sulfate types. Possibilities as surfactants of the sulfonate type are, by preference, $C_{9-13}$ alkylbenzenesulfonates, olefinsulfonates, i.e. mixtures of alkene- and hydroxyalkanesulfonates, and disulfonates, for example such as those obtained from $C_{12-18}$ monoolefins having an end-located or internal double bond, by sulfonation with gaseous sulfur trioxide and subsequent alkaline or acid hydrolysis of the sulfonation products. Also suitable are alkanesulfonates that are obtained from $C_{12-18}$ alkanes, for example by sulfochlorination or sulfoxidation with subsequent hydrolysis and neutralization. The esters of α-sulfo fatty acids (estersulfonates), e.g. the α-sulfonated methyl esters of hydrogenated coconut, palm kernel, or tallow fatty acids, are likewise suitable.

Further suitable anionic surfactants are sulfonated fatty acid glycerol esters. "Fatty acid glycerol esters" are to be understood as the mono-, di- and triesters, and mixtures thereof, that are obtained during the production by esterification of a monoglycerol with 1 to 3 mol fatty acid, or upon transesterification of triglycerides with 0.3 to 2 mol glycerol. Preferred sulfonated fatty acid glycerol esters are the sulfonation products of saturated fatty acids having 6 to 22 carbon atoms, for example hexanoic acid, octanoic acid, decanoic acid, myristic acid, lauric acid, palmitic acid, stearic acid, or behenic acid.

Preferred alk(en)yl sulfates are the alkali, and in particular sodium, salts of the sulfuric acid semi-esters of the $C_{12}$-$C_{18}$ fatty alcohols, for example from coconut fatty alcohol, tallow fatty alcohol, lauryl, myristyl, cetyl, or stearyl alcohol, or the $C_{10}$-$C_{20}$ oxo alcohols, and those semi-esters of secondary alcohols of those chain lengths. Additionally preferred are alk(en)yl sulfates of the aforesaid chain length that contain a synthetic straight-chain alkyl radical produced on a petrochemical basis, which possess a breakdown behavior analogous to those appropriate compounds based on fat-chemistry raw materials. For purposes of washing technology, the $C_{12}$-$C_{16}$ alkyl sulfates and $C_{12}$-$C_{15}$ alkyl sulfates, as well as $C_{14}$-$C_{15}$ alkyl sulfates, are preferred. 2,3-Alkyl sulfates that can be obtained, for example, as commercial products of the Shell Oil Company under the name DAN®, are also suitable anionic surfactants.

The sulfuric acid monoesters of straight-chain or branched $C_{7-21}$ alcohols ethoxylated with 1 to 6 mol ethylene oxide, such as 2-methyl-branched $C_{9-11}$ alcohols having an average of 3.5 mol ethylene oxide (EO) or $C_{12-18}$ fatty alcohols having 1 to 4 EO, are also suitable. Because of their high foaming characteristics they are used in cleaning agents only in relatively small quantities, for example in quantities from 1 to 5 wt %.

Other suitable anionic surfactants are also the salts of alkylsulfosuccinic acid, which are also referred to as sulfosuccinates or as sulfosuccinic acid esters and represent the monoesters and/or diesters of sulfosuccinic acid with alcohols, preferably fatty alcohols, and in particular ethoxylated fatty alcohols. Preferred sulfosuccinates contain $C_{8-18}$ fatty alcohol radicals or mixtures thereof. Particularly preferred sulfosuccinates contain a fatty alcohol radical that is derived from ethoxylated fatty alcohols that, considered per se, represent nonionic surfactants. Sulfosuccinates whose fatty alcohol radicals derive from ethoxylated fatty alcohols having a restricted homolog distribution are, in turn, particularly preferred. It is likewise also possible to use alk(en)ylsuccinic acid having by preference 8 to 18 carbon atoms in the alk(en)yl chain, or salts thereof.

Particularly preferred anionic surfactants are soaps. Saturated and unsaturated fatty acid soaps, such as the salts of lauric acid, myristic acid, palmitic acid, stearic acid, (hydrogenated) erucic acid, and behenic acid, are suitable, as are soap mixtures derived in particular from natural fatty acids, e.g. coconut, palm-kernel, olive-oil, or tallow fatty acids.

The anionic surfactants, including the soaps, can be present in the form of their sodium, potassium, or ammonium salts, and as soluble salts of organic bases, such as mono-, di-, or triethanolamine. The anionic surfactants are preferably present in the form of their sodium or potassium salts, in particular in the form of the sodium salts.

The concentration of anionic surfactants in preferred washing detergents or cleaning agents is 2 to 30 wt %, by preference 4 to 25 wt %, and in particular 5 to 22 wt %, based in each case on the entire washing detergent or cleaning agent.

In addition to the textile- and/or skin-care composition and the surfactants, the washing detergents or cleaning agents can contain further ingredients that further improve the aesthetic and/or applications-engineering properties of the washing detergent or cleaning agent. In the context of the present invention, preferred washing detergents or cleaning agents additionally contain one or more substances from the group of the detergency builders, bleaching agents, bleach activators, enzymes, perfumes, perfume carriers, fluorescing agents, dyes, foam inhibitors, silicone oils, anti-redeposition agents, optical brighteners, graying inhibitors, shrinkage preventers, wrinkle protection agents, color transfer inhibitors, antimicrobial active substances, germicides, fungicides, antioxidants, preservatives, corrosion inhibitors, antistatic agents, bittering agents, ironing adjuvants, repellent and impregnation agents, swelling and anti-slip agents, neutral filler salts, and UV absorbers.

Silicates, aluminum silicates (in particular zeolites), carbonates, salts of organic di- and polycarboxylic acids, and mixtures of these substances, may be mentioned in particular as detergency builders that can be contained in the washing detergents or cleaning agents.

Suitable crystalline, sheet-form sodium silicates possess the general formula $NaMSi_xO_{2x+1} \cdot H_2O$, where M denotes sodium or hydrogen, x is a number from 1.9 to 4, and y is a number from 0 to 20, and preferred values for x are 2, 3, or 4. Preferred crystalline sheet silicates of the formula indicated above are those in which. M denotes sodium and x assumes the value 2 or 3. Both β- and δ-sodium disilicates $Na_2Si_2O_5 \cdot yH_2O$ are particularly preferred.

Also usable are amorphous sodium silicates having a $Na_2O:SiO_2$ modulus from 1:2 to 1:3.3, preferably 1:2 to 1:2.8, and in particular 1:2 to 1:2.6, which are dissolution-delayed and exhibit secondary washing properties. The dissolution delay as compared with conventional amorphous sodium silicates can have been brought about in various ways, for example by surface treatment, compounding, compacting/densification, or overdrying. In the context of this invention, the term "amorphous" is also understood to mean "X-amorphous." In other words, in X-ray diffraction experiments the silicates yield not the sharp X-ray reflections that are typical of crystalline substances, but at most one or more maxima in the scattered X radiation that have a width of several degree units of the diffraction angle. Particularly good builder properties can, however, very easily be obtained even if the silicate particles yield blurred or even sharp diffraction maxima in electron beam diffraction experiments. This may be interpreted to mean that the products comprise microcrystalline regions 10 to several hundred nm in size, values of up to a maximum of 50 nm, and in particular a maximum of 20 nm, being preferred. Densified/compacted amorphous silicates, compounded amorphous silicates, and overdried X-amorphous silicates are particularly preferred.

The finely crystalline synthetic zeolite containing bound water that is used is by preference zeolite A and/or zeolite P. Zeolite MAP® (commercial product of the Crosfield Co.) is particularly preferred as zeolite P. Also suitable, however, are zeolite X as well as mixtures of A, X, and/or P. Also commercially available and preferably usable in the context of the present invention is, for example, a co-crystal of zeolite X and zeolite A (approx. 80 wt % zeolite X) that is marketed by the Sasol company under the trade name VEGOBOND AX® and can be described by the formula

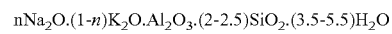

$nNa_2O.(1-n)K_2O.Al_2O_3.(2-2.5)SiO_2.(3.5-5.5)H_2O$ n=0.90-1.0

The zeolite can be used as a spray-dried powder or also as an undried stabilized suspension still moist as manufactured. In the event the zeolite is used as a suspension, it can contain small additions of nonionic surfactants as stabilizers, for example 1 to 3 wt %, based on the zeolite, of ethoxylated $C_{12}$-$C_{18}$ fatty alcohols having 2 to 5 ethylene oxide groups, $C_{12}$-$C_{14}$ fatty alcohols having 4 to 5 ethylene oxide groups, or ethoxylated isotridecanols. Suitable zeolites exhibit an average particle size of less than 10 μm (volume distribution; measurement method: Coulter Counter), and contain by preference 18 to 22 wt %, in particular 20 to 22 wt %, bound water.

Use of the commonly known phosphates as builder substances is also possible, of course, provided such use is not to be avoided for environmental reasons. The sodium salts of the orthophosphates, of the pyrophosphates, and in particular of the tripolyphosphates are particularly suitable.

Organic builders that can be present in the washing detergents or cleaning agents encompass polycarboxylate polymers such as polyacrylates and acrylic acid/maleic acid copolymers, polyaspartates, and monomeric polycarboxylates such as citrates, gluconates, succinates, or malonates, which by preference are used as sodium salts.

Among the compounds that serve as bleaching agents and yield $H_2O_2$ in water, sodium perborate tetrahydrate and sodium perborate monohydrate are particularly important. Other usable bleaching agents are, for example, sodium percarbonate, peroxypyrophosphates, citrate perhydrates, and peracid salts or peracids that yield $H_2O_2$, such as perbenzoates, peroxophthalates, diperazelaic acid, phthaloimino peracid, or diperdodecanedioic acid.

To achieve an improved bleaching effect when washing at temperatures of 60° C. and below, bleach activators can be incorporated into the washing detergents or cleaning agents.

Compounds that, under perhydrolysis conditions, yield aliphatic peroxycarboxylic acids having by preference 1 to 10 carbon atoms, in particular 2 to 4 carbon atoms, and/or optionally substituted perbenzoic acid, can be used as bleach activators. Substances that carry O- and/or N-acyl groups having the aforesaid number of carbon atoms, and/or that carry optionally substituted benzoyl groups, are suitable. Multiply acylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetyl glycoluril (TAGU), N-acylimides, in particular N-nonanoylsuccinimide (NOSI), acylated phenolsulfonates, in particular n-nonanoyl- or isononanoyloxybenzenesulfonate (n- or iso-NOBS), carboxylic acid anhydrides, in particular phthalic acid anhydride, acylated polyvalent alcohols, in particular triacetin, ethylene glycol diacetate, and 2,5-diacetoxy-2,5-dihydrofuran, are preferred.

In addition to or instead of the conventional bleach activators, so-called bleach catalysts can also be incorporated into the washing detergents or cleaning agents. These substances are bleach-intensifying transition-metal salts or transition-metal complexes such as, for example, Mn, Fe, Co, Ru, or Mo salt complexes or carbonyl complexes. Mn, Fe, Co, Ru, Mo, Ti, V, and Cu complexes having nitrogen-containing tripod ligands, as well as Co, Fe, Cu, and Ru amine complexes, are also applicable as bleach catalysts.

The washing detergent or cleaning agent can contain enzymes, in encapsulated form and/or directly in the washing detergent or cleaning agent. Suitable enzymes are, in particular, those in the classes of hydrolases, such as proteases, esterases, lipases or lipolytically active enzymes, amylases, cellulases and other glycosyl hydrolases, hemicellulase, cutinases, β-glucanases, oxidases, peroxidases, perhydrolases, mannanases, and/or laccases, and mixtures of the aforesaid enzymes. All these hydrolases contribute, in the laundry, to the removal of stains such as protein-, grease-, or starch-containing stains, and graying. Cellulases and other glycosyl hydrolases can moreover contribute to color retention and to enhanced textile softness by removing pilling and microfibrils. Oxidoreductases can also be used for bleaching and to inhibit color transfer. Enzymatic active substances obtained from bacterial strains or fungi, such as *Bacillus subtilis, Bacillus licheniformis, Streptomyceus griseus*, and *Humicola insolens*, are particularly suitable. Proteases of the subtilisin type, and in particular proteases obtained from *Bacillus lentus*, are preferably used. Enzyme mixtures, for example of protease and amylase or protease and lipase or lipolytically active enzymes, or protease and cellulase, or of cellulase and lipase or lipolytically active enzymes, or of protease, amylase, and lipase or lipolytically active enzymes, or protease, lipase or lipolytically active enzymes, and cellulase, but in particular protease- and/or lipase-containing mixtures or mixtures with lipolytically active enzymes, are of particular interest in this context. Examples of such lipolytically active enzymes are the known cutinases. Peroxidases or oxidases have also proven suitable in certain cases. The suitable amylases include, in particular, α-amylases, isoamylases, pullulanases, and pectinases. Cellobiohydrolases, endoglucanases, and β-glucosidases, which are also called cellobiases, and mixtures thereof, are preferably used as cellulases. Because different types of cellulase differ in terms of their CMCase and avicelase activities, the desired activities can be adjusted by means of controlled mixtures of the cellulases.

The enzymes can be adsorbed onto carrier materials in order to protect them from premature breakdown. The proportion of enzymes or enzyme granules directly in the washing detergent or cleaning agent can be, for example, approximately 0.01 to 5 wt %, by preference 0.12 to approximately 2.5 wt %.

It may also be preferred, however, for example in special washing detergents or cleaning agents for consumers with allergies and/or sensitive skin, for the washing detergent or cleaning agent to contain no enzymes.

In an embodiment, the washing detergent or cleaning agent contains, if applicable, one or more perfumes in a quantity of usually up to 10 wt %, by preference 0.5 to 7 wt %, in particular 1 to 3 wt %. The quantity of perfume used also depends on the type of washing detergent or cleaning agent. It is particularly preferred, however, that the perfume be introduced into the washing detergent or cleaning agent via the textile- and/or skin-care composition. It is nevertheless also possible for the washing detergent or cleaning agent to contain perfume that is not introduced into the washing detergent or cleaning agent via the textile- and/or skin-care composition.

In order to improve the aesthetic impression of the washing detergents or cleaning agents, they can be colored (also only in part, if applicable) with suitable dyes. Preferred dyes, the selection of which will present no difficulty whatsoever to one skilled in the art, possess excellent shelf stability and insensitivity to the other ingredients of the washing detergents or cleaning agents and to light, and no pronounced substantivity with respect to textile fibers, in order not to color them.

Appropriate foam inhibitors that can be used in the washing detergents or cleaning agents are, for example, soaps, paraffins, or silicone oils, which optionally can be applied onto carrier materials.

Suitable soil release polymers, which are also referred to as "anti-redeposition agents," are, for example, nonionic cellulose ethers such as methyl cellulose and methylhydroxypropyl cellulose having a 15 to 30 wt % proportion of methoxy groups and a 1 to 15 wt % proportion of hydroxypropyl groups, based in each case on the nonionic cellulose ethers, as well as polymers, known from the existing art, of phthalic acid and/or terephthalic acid and of their derivatives, in particular polymers of ethylene terephthalates and/or polyethylene and/or polypropylene glycol terephthalates or anionically and/or nonionically modified derivatives thereof. Suitable derivatives encompass the sulfonated derivates of phthalic acid polymers and terephthalic acid polymers. A further class of suitable soil release polymers, in particular for cotton-containing textiles, is represented by modified, for example alkoxylated and/or quaternized and/or oxidized, polyamines. The polyamines are, for example, polyalkyleneamines such as polyethyleneamines, or polyalkyleneimines such as polyethyleneimines. Preferred examples of this class of soil release polymers are ethoxylated polyethyleneimines and ethoxylated polyethyleneamines.

Optical brighteners (so-called "whiteners") can be added to the washing detergents or cleaning agents in order to eliminate graying and yellowing of the treated textile fabrics. These substances absorb onto the fibers and cause brightening and a simulated bleaching effect by converting invisible ultraviolet radiation into longer-wave visible light, the ultraviolet light absorbed from sunlight being emitted as slightly bluish fluorescence and resulting, with the yellow tone of the grayed or yellowed laundry, in pure white. Suitable compounds derive, for example, from the substance classes of the 4,4'-diamino-2,2'-stilbenedisulfonic acids (flavonic acids), 4,4'-distyrylbiphenyls, methylumbelliferones, cumarins, dihydroquinolinones, 1,3-diarylpyrazolines, naphthalic acid imides, benzoxazole, benzisoxazole, and benzimidazole systems, and pyrene derivatives substituted with heterocycles. The optical brighteners are usually used in quantities of between 0 and 0.3 wt % based on the finished washing detergent or cleaning agent.

The purpose of graying inhibitors is to keep dirt released from the fibers suspended in the bath, thus preventing the dirt from redepositing. Water-soluble colloids, usually organic in nature, are suitable for this, for example size, gelatin, salts of ethersulfonic acids of starch or of cellulose, or salts of acid sulfuric acid esters of cellulose or starch. Water-soluble polyamides containing acid groups are also suitable for this purpose. Soluble starch preparations, and starch products other than those mentioned above, can also be used, e.g. degraded starch, aldehyde starches, etc. Polyvinylpyrrolidone is also usable. It is preferred, however, to use cellulose ethers such as carboxymethyl cellulose (Na salt), methyl cellulose, hydroxyalkyl cellulose, and mixed ethers such as methylhydroxyethyl cellulose, methylhydroxypropyl cellulose, methylcarboxymethyl cellulose, and mixtures thereof, in quantities from 0.1 to 5 wt % based on the washing detergents or cleaning agents.

In order effectively to suppress dye dissolution and/or dye transfer onto other textiles during the washing and/or cleaning of colored textiles, the washing detergent or cleaning agent can contain a color transfer inhibitor. It is preferred that the color transfer inhibitor be a polymer or copolymer of cyclic amines such as, for example, vinylpyrrolidone and/or vinylimidazole. Polymers suitable as a color transfer inhibitor encompass polyvinylpyrrolidone (PVP), polyvinylimidazole (PVI), copolymers of vinylpyrrolidone and vinylimidazole (PVP/PVI), polyvinyl pyridine-N oxide, poly-N-carboxymethyl-4-vinylpyridium chloride, and mixtures thereof. It is particularly preferred to use polyvinylpyrrolidone (PVP), polyvinylimidazole (PVI), or copolymers of vinylpyrrolidone and vinylimidazole (PVP/PVI) as a color transfer inhibitor. The polyvinylpyrrolidones (PVP) that are used preferably possess an average molecular weight from 2,500 to 400,000, and are available commercially from ISP Chemicals as PVP K 15, PVP K 30, PVP K 60, or PVP K 90, or from BASF as Sokalan® HP 50 or Sokalan® HP 53. The copolymers of vinylpyrrolidone and vinylimidazole (PVP/PVI) that are used preferably have a molecular weight in the range from 5000 to 100,000. A PVP/PVI copolymer is available commercially, for example, from BASF under the designation Sokalan® HP 56.

The quantity of color transfer inhibitor, based on the total quantity of the washing detergent or cleaning agent, is preferably from 0.01 to 2 wt %, by preference from 0.05 to 1 wt %, and more preferably from 0.1 to 0.5 wt %.

Alternatively, however, enzymatic systems encompassing a peroxidase and hydrogen peroxide or a substance yielding hydrogen peroxide in water, can be used as a color transfer inhibitor. The addition of a mediator compound for the peroxidase, for example an acetosyringone, a phenol derivative, or a phenothiazine or phenoxazine, is preferred in this case; the aforementioned polymeric color transfer inhibitors can also be used additionally.

Because textile fabrics, in particular those made of rayon, viscose, cotton, and mixtures thereof, can tend to wrinkle because the individual fibers are sensitive to bending, kinking, pressing, and squeezing perpendicularly to the fiber direction, the agents according to the present invention can contain synthetic wrinkle-protection agents. These include, for example, synthetic products based on fatty acids, fatty acid esters, fatty acid amides, fatty acid alkylol esters, or fatty acid alkylolamides, or fatty alcohols that are usually reacted with ethylene oxide, or products based on lecithin or modified phosphoric acid esters.

In order to counteract microorganisms, the washing detergents or cleaning agents can contain antimicrobial active substances. A distinction is made here, depending on the antimicrobial spectrum and mechanism of action, between bacteriostatics and bactericides, fungistatics and fungicides, etc. Important substances from these groups are, for example, benzalkonium chlorides, alkylarylsulfonates, halogen phenols, and phenol mercuric acetate; these compounds can also be entirely dispensed with in the washing detergents or cleaning agents according to the present invention.

The washing detergents or cleaning agents according to the present invention can contain preservatives, preferably only those that possess little or no skin-sensitizing potential being used. Examples are sorbic acid and its salts, benzoic acid and its salts, salicylic acid and its salts, phenoxyethanol, 3-iodo-2-propynylbutyl carbamate, sodium N-(hydroxymethyl) glycinate, biphenyl-2-ol, and mixtures thereof.

The washing detergents or cleaning agents can contain antioxidants in order to prevent undesired changes, caused by the action of oxygen and other oxidative processes, to the washing detergents or cleaning agents and/or to the treated textile fabrics. This class of compounds includes, for example, substituted phenols, hydroquinones, catechols, and aromatic amines, as well as organic sulfides, polysulfides, dithiocarbamates, phosphites, phosphonates, and vitamin E.

Increased wearing comfort can result from the additional use of antistatic agents that are added to the washing detergents or cleaning agents. Antistatic agents increase the surface conductivity and thus make possible improved dissipation of charges that have formed. External antistatic agents are usually substances having at least one hydrophilic molecule ligand, and yield a more or less hygroscopic film on the surfaces. These usually surface-active antistatic agents can be subdivided into nitrogen-containing (amines, amides, quaternary ammonium compounds), phosphorus-containing (phosphoric acid esters), and sulfur-containing antistatic agents (alkylsulfonates, alkyl sulfates). Lauryl- (or stearyl-)-dimethylbenzylammonium chlorides are likewise suitable as antistatic agents for textiles or as an additive to washing detergents or cleaning agents, an avivage effect additionally being achieved.

In order to improve the rewettability of the treated textile fabrics and to facilitate ironing of the treated textile fabrics, silicone derivatives, for example, can be used in the washing detergents or cleaning agents. These additionally improve the rinsing behavior of the washing detergents or cleaning agents thanks to their foam-inhibiting properties. Preferred silicone derivatives are, for example, polydialkyl- or alkylarylsiloxanes in which the alkyl groups have one to five carbon atoms and are entirely or partly fluorinated. Preferred silicones are polydimethylsiloxanes, which optionally can be derivatized and are then aminofunctional or quaternized or have Si—OH, Si—H, and/or Si—Cl bonds. The viscosities of the preferred silicones are in the range between 100 and 100,000 mPas at 25° C.; the silicones can be used in quantities between 0.2 and 5 wt % based on the entire washing detergent or cleaning agent.

Lastly, the washing detergents or cleaning agents can also contain UV absorbers, which are absorbed onto the treated textile fabrics and improve the light-fastness of the fibers. Compounds that exhibit these desired properties are, for example, the compounds that act by radiationless deactivation, and derivatives of benzophenone having substituents in the 2- and/or 4-position. Also suitable are substituted benzotriazoles, acrylates phenyl-substituted in the 3-position (cinnamic acid derivatives) optionally having cyano groups in the 2-position, salicylates, organic Ni complexes, and natural substances such as umbelliferone and endogenbus urocanic acid.

Substances that complex heavy metals can be used in order to avoid the heavy-metal-catalyzed breakdown of certain washing-detergent ingredients. Suitable heavy metal complexing agents are, for example, the alkali salts of ethylenediaminetetraacetic acid (EDTA) or of nitrilotriacetic acid (NTA), as well as alkali-metal salts of anionic polyelectrolytes such as polymaleates and polysulfonates.

A preferred class of complexing agents is the phosphonates, which are contained in preferred washing detergents or cleaning agents in quantities from 0.01 to 2.5 wt %, by preference 0.02 to 2 wt %, and in particular from 0.03 to 1.5 wt %. Among these preferred compounds are, in particular, organophosphonates such as, for example, 1-hydroxyethane-1,1-diphosphonic acid (HEDP), aminotri(methylenephosphonic acid) (ATMP), diethylenetriamine penta(methylenephosphonic acid) (DTPMP or DETPMP), and 2-phosphonobutane-1,2,4-tricarboxylic acid (PBS-AM), which are usually used in the form of their ammonium or alkali-metal salts.

Neutral filler salts such as sodium sulfate or sodium carbonate can additionally be contained in the solid washing detergents or cleaning agents.

The washing detergents or cleaning agents according to the present invention can be used in particular for the cleaning and conditioning of textile fabrics.

For manufacture of the washing detergents or cleaning agents according to the present invention, firstly the washing detergent or cleaning agent without the textile- and/or skin-care compound is manufactured using known processes, which can encompass e.g. drying steps, mixing steps, compaction steps, shaping steps, and/or post-addition of heat-sensitive ingredients. The product thus obtained is then mixed with a solid textile- and/or skin-care composition according to the present invention. For the manufacture of shaped washing-detergent or cleaning-agent elements, further compaction and/or shaping steps can follow the mixing step.

While particular embodiments of the present invention have been illustrated and described, it would be obvious to those skilled in the art that various other changes and modifications can be made without departing from the spirit and scope of the invention.

Other than where otherwise indicated, or where required to distinguish over the prior art, all numbers expressing quantities of ingredients herein are to be understood as modified in all instances by the term "about". As used herein, the words "may" and "may be" are to be interpreted in an open-ended, non-restrictive manner. At minimum, "may" and "may be" are to be interpreted as definitively including, but not limited to, the composition, structure, or act recited.

As used herein, and in particular as used herein to define the elements of the claims that follow, the articles "a" and "an" are synonymous and used interchangeably with "at least one" or "one or more," disclosing or encompassing both the singular and the plural, unless specifically defined herein otherwise. The conjunction "or" is used herein in both in the conjunctive and disjunctive sense, such that phrases or terms conjoined by "or" disclose or encompass each phrase or term alone as well as any combination so conjoined, unless specifically defined herein otherwise.

The description of a group or class of materials as suitable or preferred for a given purpose in connection with the invention implies that mixtures of any two or more of the members of the group or class are equally suitable or preferred. Description of constituents in chemical terms refers unless otherwise indicated, to the constituents at the time of addition to any combination specified in the description, and does not necessarily preclude chemical interactions among the constituents of a mixture once mixed. Steps in any method disclosed or claimed need not be performed in the order recited, except as otherwise specifically disclosed or claimed.

Changes in form and substitution of equivalents are contemplated as circumstances may suggest or render expedient. Although specific terms have been employed herein, such terms are intended in a descriptive sense and not for purposes of limitation.

The following Examples further illustrate the preferred embodiments within the scope of the present invention, but are not intended to be limiting thereof. It is understood that the examples and embodiments described herein are for illustrative purposes only and that various modifications or changes in light thereof will be suggested to one skilled in the art without departing from the scope of the present invention. The appended claims therefore are intended to cover all such changes and modifications that are within the scope of this invention.

EXAMPLES

Example 1

Water-Soluble Particle

For the manufacture of a textile- and/or skin-care composition E1 according to the present invention, industrial sugar having a particle size from 1 to 3 mm was colored red using Pigment Red 5 dye.

Water-Insoluble Particle

Concurrently, granulated bentonite particles (Laundrosil® DGA of Südchemie) having a particle size from 1 to 3 mm were colored red using the same dye (Pigment Red 5) as for the industrial sugar, and then sprayed with a perfume. The two particles were then mixed at a ratio such that the finished textile- and/or skin-care composition according to the present invention contained 52 wt % industrial sugar, 45 wt % bentonite, 2.9 wt % perfume, and 0.1 wt % dye.

For comparison of the scent intensity of a conventional liquid fabric softener (textile-softening diesterquat concentration: 15 wt %) with the solid textile- and/or skin-care compositions, terry cloth fabric was treated in a washing machine (Miele Novotronic W 985) on the one hand with a commercially obtainable solid washing detergent and the conventional fabric softener, and on the other hand with the same washing detergent and the solid textile- and/or skin-care compositions E1. After line drying, the scent intensity was determined.

| Composition | Damp, freshly washed laundry | Dried laundry, after 1 day | Dried laundry, after 7 days |
|---|---|---|---|
| Comparison | 1.2 | 0.9 | 0.7 |
| E1 | 2.3 | 1.1 | 1.1 |

Score: 0 = weak to 4 = strong
No. of persons evaluating: 7

The textile- and/or skin-care compositions according to the present invention furthermore exhibited a textile-softening effect as compared with water. The fabrics treated with water and with the textile- and/or skin-care composition had been handled for that purpose, after treatment and line drying, by a panel of five persons. While the softness value obtained for fabrics treated with water was 1.9 (0=hard to 6=soft), fabric treated with E1 yielded a softness value of 3.0.

In addition, the textile- and/or skin-care compositions according to the present invention are capable of reducing the hardness of water. This determination was made using Total Hardness test sticks (Merck) in accordance with the manufacturer's instructions.

Better results for the softness value were obtained for textile- and/or skin-care compositions according to the present invention in which the water-insoluble bentonite particles had additionally been sprayed or treated with a textile-softening compound (E2: 4 wt % polydimethylsiloxane; E3: 5 wt % Polyquaternium-7; and E4: 5 wt % Polyquaternium-10) (the wt % values indicate the quantity by weight of the textile-softening compounds in the finished textile- and/or skin-care compound). The quantities of industrial sugar or bentonite in the finished textile- and/or skin-care composition were correspondingly reduced by 2 wt % and 2.5 wt %, respectively.

A further textile- and/or skin-care composition was obtained, in a manner analogous to that described above, by additionally spraying the water-insoluble bentonite particles with a solution that contained the optical brightener Tinopal® CBS-X (of Ciba) and then mixing those particles with the water-soluble particles. The finished textile- and/or skin-care composition E5 according to the present invention contained 52 wt % industrial sugar, 44.95 wt % bentonite, 2.9 wt % perfume, 0.05 wt % optical brightener, and 0.1 wt % dye. Textile fabrics that had been treated with textile- and/or skin-care composition E5 exhibited an increased softness impression.

For the manufacture of a washing detergent or cleaning agent according to the present invention, a solid, unperfumed washing detergent or cleaning agent was mixed with 10 wt % (based on the total quantity of finished washing detergent or cleaning agent) of textile- and/or skin-care composition E1.

The washing detergent or cleaning agent according to the present invention exhibited good cleaning and conditioning properties.

Lime deposits on the laundry and/or deposits or residues in the bleach dispenser of the washing machines were not observed either with separate utilization of the textile- and/or skin-care composition or when introduced into a washing detergent or cleaning agent.

What is claimed:

1. A solid particulate textile- and/or skin-care composition, comprising a mixture of water-soluble particles and water-insoluble particles,
   the water-soluble particles comprising a carbohydrate carrier selected from the group consisting of dextrose, fructose, galactose, isoglucose, glucose, sucrose, raffinose, and mixtures thereof,
   the water-insoluble particles comprising a water-insoluble carrier and at least one textile- and/or skin-care compound carried on said water-insoluble carrier,
   wherein the at least one textile- and/or skin-care compound comprises a perfume and a textile softening compound, the perfume comprising ≥1% by weight of the composition and the textile softening compound is selected from the group consisting of quaternary ammonium compounds, and
   wherein the water-soluble particles and the water-insoluble particles each have a particle size in the range of 0.6 mm to 30 mm.

2. The composition of claim 1, wherein the water-soluble particles further comprises one or more carriers selected from the group consisting of inorganic alkali metal salts, organic alkali metal salts, inorganic alkaline earth metal salts, organic alkaline earth metal salts, organic acids, silicates, and mixtures thereof.

3. The composition of claim 1, comprising 10% to 90% by weight of the water-soluble particles.

4. The composition of claim 3, comprising 40% to 60% by weight of the water-soluble particles.

5. The composition of claim 1, wherein the water-insoluble carrier is a textile-softening clay.

6. The composition of claim 5, wherein the textile-softening clay is a bentonite.

7. The composition of claim 1, wherein the at least one textile- and/or skin-care compound further comprises an agent selected from the group consisting of fluorescing agents, anti-redeposition agents, optical brighteners, graying inhibitors, shrinkage preventers, wrinkle protection agents, color transfer inhibitors, antimicrobial active substances, germicides, fungicides, antioxidants, antistatic agents, ironing adjuvants, UV absorbers, repellent agents, impregnation agents, skin-care compounds, perfumes, and mixtures thereof.

8. The composition of claim 1, wherein the perfume comprises 1% to 20% by weight of the composition.

9. The composition of claim 8, wherein the perfume comprises 1% to 10% by weight of the composition.

10. The composition of claim 9, wherein the perfume comprises 2% to 7% by weight of the composition.

11. The composition of claim 1, wherein the at least one textile- and/or skin-care compound further comprises a polysiloxane.

12. The composition of claim 1, wherein the water-insoluble particles further comprise an ingredient selected from the group consisting of dyes, fillers, luster agents, and mixtures thereof.

13. The composition of claim 1, wherein the water-soluble particles and/or the water-insoluble particles have a particle size in the range of 0.8 mm to 20 mm.

14. The composition of claim 13, wherein the water-soluble particles and/or the water-insoluble particles have a particle size in the range of 1 mm to 10 mm.

15. A method for manufacturing a solid textile- and/or skin-care composition according to claim 1, comprising mixing a water-soluble particle and a water-insoluble particle, the water-soluble particle comprising a carbohydrate, the water-insoluble particle comprising a water-insoluble carrier and a textile- and/or skin-care compound carried on said water-insoluble carrier, wherein the textile- and/or skin-care compound comprises a perfume.

16. A washing detergent or cleaning agent comprising the composition of claim 1 and at least one surfactant.

17. A washing detergent or cleaning agent, comprising a mixture of a solid washing detergent or cleaning agent and the composition of claim 1.

18. The composition of claim 1, wherein the water-soluble particles comprise sucrose crystals having a particle size of 1 mm to 2 mm.

19. A solid particulate textile- and/or skin-care composition, comprising a mixture of water-soluble particles and water-insoluble particles, the particles being in the form of powder, granulate, or agglomerates, the water-soluble particles consisting of a carbohydrate carrier selected from the group consisting of dextrose, fructose, galactose, isoglucose, glucose, sucrose, raffinose, and mixtures thereof, optionally one or more additional water-soluble carriers selected from the group consisting of inorganic alkali metal salts, organic alkali metal salts, inorganic alkaline earth metal salts, organic alkaline earth metal salts, organic acids, silicates, and mixtures thereof, and optionally one or more ingredients selected from the group consisting of dyes, fillers, luster agents, and mixtures thereof, the water-insoluble particles consisting of a water-insoluble carrier, a perfume, a textile softening compound, optionally one or more textile- and/or skin-care compounds selected from the group consisting of fluorescing agents, anti-redeposition agents, optical brighteners, graying inhibitors, shrinkage preventers, wrinkle protection agents, color transfer inhibitors, antimicrobial active substances, germicides, fungicides, antioxidants, antistatic agents, ironing adjuvants, UV absorbers, repellent agents, impregnation agents, skin-care compounds, and mixtures thereof, and optionally one or more ingredients selected from the group consisting of dyes, fillers, luster agents, and mixtures thereof, wherein the perfume comprises $\geq 1\%$ by weight of the composition and the textile softening compound is selected from the group consisting of quaternary ammonium compounds wherein the powder or granulate textile- and/or skin-care composition is obtained by mixing the water-soluble and water-insoluble particles.

* * * * *